United States Patent [19]

Gilbert et al.

[11] Patent Number: 5,466,898
[45] Date of Patent: Nov. 14, 1995

[54] STETHOSCOPE ISOLATION SYSTEM

[76] Inventors: Edwin E. Gilbert, 1512 Severn Ave., Metairie, La. 70001; Timothy J. Foret, 557 Hospital Dr., Raceland, La. 70394

[21] Appl. No.: 855,613

[22] Filed: Mar. 20, 1992

[51] Int. Cl.$^6$ ..................................................... A61B 7/02
[52] U.S. Cl. ................................................................ 181/131
[58] Field of Search ...................................... 181/130, 131, 181/137; 381/67; 374/158, 209

[56] References Cited

U.S. PATENT DOCUMENTS

| | | | |
|---|---|---|---|
| 738,960 | 9/1903 | Vaughn et al. | 374/158 |
| 2,049,729 | 8/1936 | Berkowitz | 229/74 |
| 3,678,751 | 7/1972 | Mead et al. | 374/158 |
| 3,750,471 | 8/1973 | Bremer | 374/158 |
| 3,939,971 | 2/1976 | Tulis . | |
| 4,042,170 | 8/1977 | Ekman et al. . | |
| 4,116,338 | 9/1978 | Weichselbaum . | |
| 4,159,766 | 7/1979 | Kluge | 374/158 |
| 4,226,162 | 10/1980 | Ebach | 181/131 X |
| 4,401,125 | 8/1983 | Taylor et al. . | |
| 4,406,346 | 9/1983 | Pope, Jr. | 181/131 |
| 4,550,831 | 11/1985 | Whitford . | |
| 4,630,729 | 12/1986 | Hirt et al. . | |
| 4,867,265 | 9/1989 | Wright . | |
| 4,867,268 | 9/1989 | Ulert . | |
| 4,871,046 | 10/1989 | Turner . | |
| 4,998,538 | 3/1991 | Charowsky et al. . | |
| 5,002,561 | 3/1991 | Fisher . | |
| 5,163,418 | 11/1992 | Fraden et al. | 374/158 |
| 5,172,683 | 12/1992 | West | 181/131 |

*Primary Examiner*—Khanh Dang
*Attorney, Agent, or Firm*—Joseph T. Regard, Ltd.

[57] ABSTRACT

A system for preventing nosocomial infection and contamination through usage of a stethoscope, utilizing a stethoscope sleeve and fitting accessory configured to be utilized in conjunction with off-the-shelf stethoscopes and the like. A first embodiment (FIGS. 1 & 2b) includes a one-use, disposable sleeve, wherein the head or diaphragm-retaining ring is covered in its entirety, with the full covering up of the body to the ear tubes, the cover being composed of a bacterial, viral, and fluid impermeable, acoustically transparent medium. The accessory includes a spreader attachment removably affixed to the upper body of the stethoscope and containable within the sleeve when mounted on the stethoscope. In combination with the spreader attachment accessory, the system provides a sterile system for preventing infection which isolates the stethoscope from both the user as well as the patient, greatly reducing any risk of contamination. A second embodiment (FIGS. 3 & 2a), designed for reducing the spread of infection among health care workers sharing a patient dedicated instrument during reverse isolation technique, utilizes substantially the same sleeve but which further includes a handle apparatus affixed to the wishbone portion of the instrument, allowing the ear caps of the instrument to be spread for engaging and disengaging the instrument from the various health care workers, without the necessity of touching the body of the instrument during use, thereby preventing cross infection during the consequential sharing of the dedicated stethoscope by the various health care providers.

7 Claims, 3 Drawing Sheets

STETHOSCOPE ISOLATION SYSTEM

BACKGROUND OF INVENTION

1. Field of Invention

The present invention relates to systems for preventing biological infection and contamination via the promotion of aseptic and sterile techniques, utilizing a unique and innovative stethoscope sleeve and fitting accessory, in conjunction with off-the-shelf stethoscopes and the like.

The present invention provides inexpensive, reliable, and easily implemented systems for preventing infection from being spread from one observed patient or health care worker to another worker or patient, adaptable for use in conjunction with isolation, as well as reverse isolation, techniques. Such a technique would typically include a stethoscope isolation system designed for prevention of transmission of infection in isolation or reverse isolation situations.

The exemplary embodiment of the stethoscope sleeve of the present invention includes a sleeve, wherein the head or diaphragm-retaining ring is covered in its entirety, with full covering up to and affixed to the upper body of the stethoscope. The cover is composed of a bacterial, viral, and fluid impermeable, acoustically transparent medium.

The alternative embodiment of the present invention further contemplates and teaches a spreader attachment designed to be removably affixed to the ear tube area of the stethoscope. The spreader attachment is configured to be contained within the sleeve when mounted to the stethoscope.

In use, the stethoscope sleeve provides an easily implemented system for preventing nosocomial infection, wherein one merely affixes the sleeve about the stethoscope, utilizes it in a normal fashion, and removes and disposes of the sleeve prior to utilization upon another.

In combination with the spreader attachment accessory of the invention, the system provides a sterile system for preventing infection under isolation or reverse isolation techniques, wherein the provided stethoscope has attached to it the spreader accessory and then the sleeve, isolating the stethoscope from both the user as well as the patient, greatly reducing any risk of infection.

2. Prior Art & General Background

While the prior art is replete with various designs teaching accessories for preventing infection and facilitating increased performance for use with stethoscopes and the like, the prior art has failed to teach, anticipate, or suggest a system for preventing infection transfer via stethoscopes and the like, while following aseptic and/or sterile techniques, as taught in the present invention.

A list of prior patents which may be of interest is presented below:

| Patent No. | Patentee(s) | Issue Date |
| --- | --- | --- |
| 3,939,971 | Tulis | 02/24/76 |
| 4,042,170 | Ekman et al | 08/16/77 |
| 4,116,338 | Weichselbaum | 09/26/78 |
| 4,401,125 | Taylor, et al | 08/30/83 |
| 4,550,831 | Whitford | 11/05/85 |
| 4,630,729 | Hirt et al | 12/23/86 |
| 4,867,265 | Wright | 09/19/89 |
| 4,867,268 | Ulert | 09/19/89 |
| 4,871,046 | Turner | 10/03/89 |

-continued

| Patent No. | Patentee(s) | Issue Date |
| --- | --- | --- |
| 4,998,538 | Charowsky et al | 03/12/91 |
| 5,002,561 | Fisher | 03/26/91 |

For example, U.S. Pat. No. 4,867,265, issued in 1989, discloses a "precordial stethoscope cover" primarily designed for enhancing the acoustical performance of the stethoscope diaphragm system via noise inhibiting insulation surrounding the head of the stethoscope, but it also recognizes the sanitary advantages for providing an interface between the stethoscope head and the patient.

However, the '265 patent does not teach nor claim a cover which encompasses the full body of the stethoscope, but only a partial, sleeve type cover over the head, with an acoustical interface to aid in the acoustical efficiency of the stethoscope.

U.S. Pat. No. 4,867,268, also issued in 1989 and directed to a "sanitary stethoscope", contemplates a replaceable/disposable diaphragm, while recognizing that:

" . . . in the conventional use of a stethoscope by physicians, the stethoscope is not sterilized between examinations in patients.

Typically, as the stethoscope is directly applied to the skin, the diaphragm will become contaminated and thus has a potential for contaminating the next patient."

Again, while the '268 patent recognized the potential for transmission of infection utilizing a stethoscope in rounds, this device is distinguishable from the present invention in design and use in that the present invention contemplates a system to prevent infection via aseptic and/or sterile technique methods, preventing cross infection of patients as well as infection from doctor to patient and visa-versa.

The '268 system is nonetheless pertinent, at least in part, however, in that it contemplates the utilization of a cover for at least a portion of the stethoscope, namely the head.

U.S. Pat. No. 4,871,046 teaches a "disposable stethoscope head shield", which apparently has been designed specifically in view of the AIDS infection problems, teaching a stethoscope head cover and dispenser unit therefor, for quickly and easily sheathing the head with a disposable, acoustically transparent and viral impermeable material.

Again, the '046 patent is distinguishable in terms of novelty from the present invention in its construction and use, in that it contemplates only a head shield for the stethoscope, wherein there still exists the risk of infection and viral infection, and would not be permissible for use under sterile techniques.

In summary, while the prior art has contemplated the sheathing of the head of a stethoscope for a variety of contemplated purposes, including enhancing the acoustical performance of the instrument and preventing transmission of infective disease via contact with the head, none teach nor contemplate a sheathing system wherein the full body of the stethoscopes is covered, providing full protection of infection in the utilization of the stethoscope under aseptic as well as sterile infection prevention techniques.

GENERAL SUMMARY DISCUSSION OF THE INVENTION

The present invention provides a relatively inexpensive, easily implemented, and effective system for preventing contamination of a stethoscope which overcomes the limitations of the prior art set forth supra.

Heretofore, patients have had the risk of nosocomial infection via utilization of the heath care worker's own stethoscope. The only alternative heretofore being a "slave" or dedicated stethoscope provided under isolation techniques, wherein the instrument was provided for the exclusive examination of that particular patient.

However, this prior art system of dedicated stethoscopes is not completely effective, as a dedicated or "slave" stethoscope, while provided for the examination of one exclusive patient, is nonetheless utilized by any number of examining health care providers, each of which will likely touch the patient in order to, for example, take blood pressure and pulse, monitor breathing, or determine physiological symptoms such as pain, et cetera.

Thus, during the routine examination of the patient, not only is the head of the stethoscope in contact with the patient, but the body of the instrument is as well, via at least secondary contact after the health care personnel touches the patient and then removes the stethoscope via grasping the body of the instrument, contaminating it.

Utilization of a dedicated stethoscope as above with high risk patients, therefore, provides a significant risk of cross infection of the health care personnel monitoring the patient, and does not solve the problem of isolating infection.

In fact, this technique may further spread infection, as the worker utilizing the stethoscope is unaware as to the degree of contact and consequential contamination the instrument has had with the infected patient. At least with their own stethoscope, the worker would have been better appraised as to the degree of infection, and better able to monitor when it was time for sterilization of the instrument.

In contrast, the present system of the invention provides a stethoscope cover and accessory for maintaining sterile techniques while promoting aseptic infection prevention, which may be utilized in isolation techniques, as well as in a normal patient care context, as set forth supra, while preventing any contact, secondary or otherwise, with the instrument, thereby reducing the chances of contamination.

The present invention teaches the use of a sleeve with the stethoscope designed to maintain a sterile barrier, thereby reducing the risk of nosocomial infection. The present sleeve is designed to fit over all models of off-the-shelf stethoscopes, and is disclosed in two primary embodiments, namely:

(1) a one piece, fluid, bacterial, and viral impermeable barrier, covering the head to upper body of the stethoscope, sheathing same, with the upper end removably affixed to the upper body via an adhesive or the like, for preventing contamination during routine examination by the health care worker utilizing his or her own stethoscope to examine multiple patients; and (2) a system designed for preventing the spread of infection among health care workers sharing an instrument during reverse isolation technique, utilizing the same sleeve as denoted above, further including a handle apparatus that affixes to the wishbone portion of the instrument, allowing the ear caps of the instrument to be spread for engaging and disengaging the instrument from the various health care workers, without the necessity of touching the body of the instrument during use, thereby preventing cross infection during the consequential sharing of the dedicated stethoscope by the various monitoring nurses and physicians.

It is therefore an object of the present invention to provide a system for preventing the transmission of infection from one patient to another via a contaminated stethoscope, isolating the instrument in a disposable, biologically impermeable sleeve which may be removed and changed between examinations.

It is another object of the present invention to provide a system for preventing the cross infection through health care workers and the like dispensing with the necessity of sharing a stethoscope during the practice of isolation techniques, wherein there is provided a sleeve for covering the head and body of the stethoscope, and further teaching the utilization of an apparatus configured for spreading the wish bone portion of the body of the stethoscope, allowing the mounting and dismounting of same by the user without the necessity of actually touching the instrument, preventing its contamination, thereby allowing the use of one's own stethoscope.

It is another object of the present invention to provide a stethoscope isolation system and technique which is compatible with aseptic and sterile techniques of preventing infection.

It is still another object of the present invention to provide a system for preventing contamination of stethoscopes and like instruments which is effective, inexpensive to manufacture, disposable, and easy to implement.

It is still another object of the present invention to provide a system for utilization of a common stethoscope among health care workers under isolation conditions, which prevents cross infection.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED, EXEMPLARY EMBODIMENTS

Figure 1:
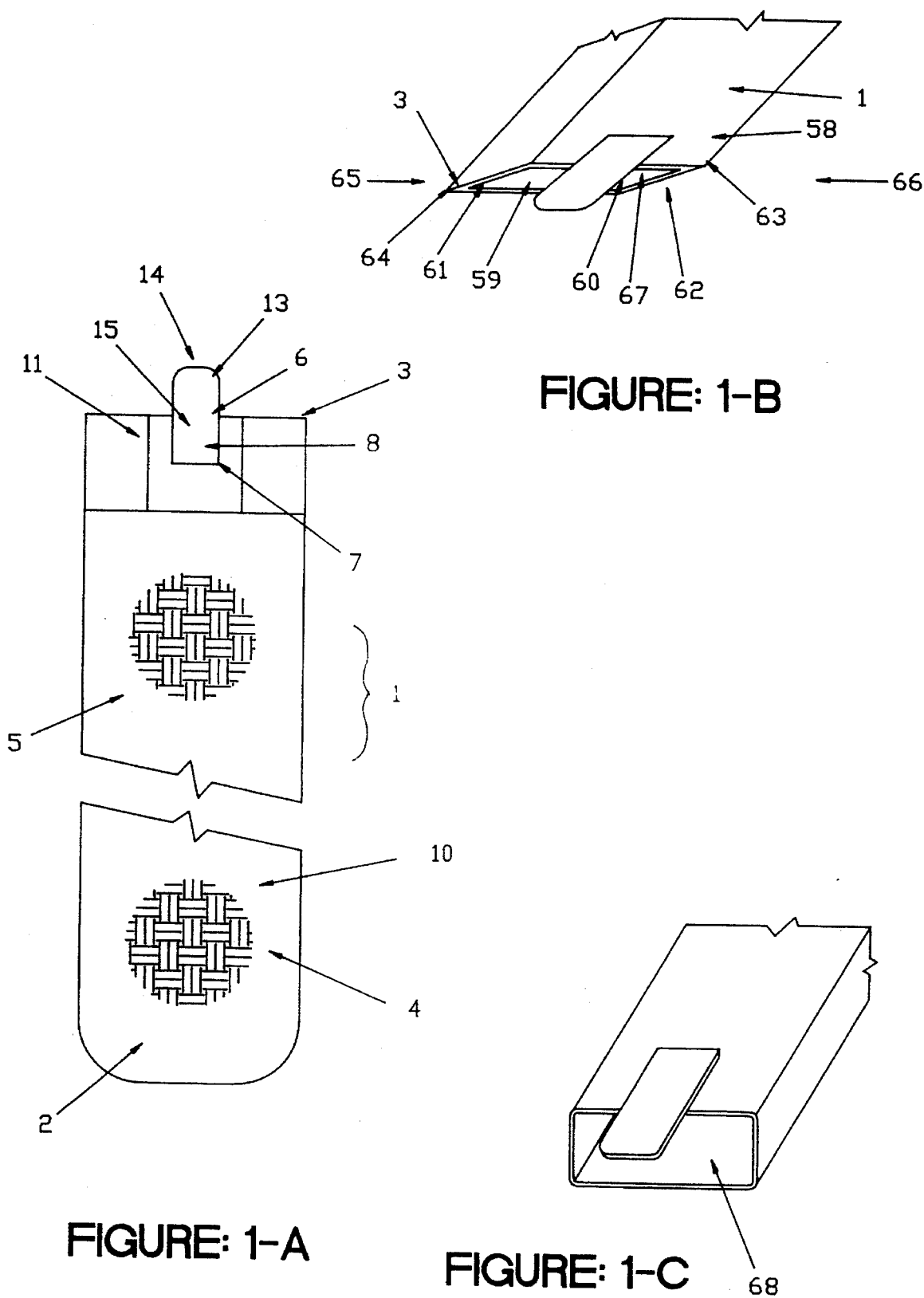
FIGS. 1a–1c are frontal, partially cutaway view of the preferred embodiment of the stethoscope isolation system of the present invention, illustrating the sheath of the present invention, and further illustrating the expansion frame (58), and its use in expanding the mouth (67) of the sleeve (1) of the present invention.

As can be seen in FIGS. 1a–1c, the stethoscope isolation system of the preferred, exemplary embodiment of the present invention, designed for practicing aseptic or "clean" technique, includes a sleeve 1 wherein there is included first (2) and second (3) ends. The sleeve 1 has formed therein a cavity 4 for accepting the lower end of a stethoscope, the cavity being surrounded by a wall 5 of fluid, bacterial, and virally impermeable fabric, paper, or the like, composed of first (10) and second (11) sides.

Affixed to the second, open end 3 of the sleeve 1 is a portion 8 of adhesive strip 6, adhered 7 to the second side 11 of wall 5. The adhesive strip 6 further includes a crease 15 and a removable adhesive 13 having an adhesive covering strip 14 thereon.

FIGS. 1b and 1c illustrate the expansion frame of the present invention in its closed and open positions, respectively. As shown in its exemplary embodiment, the frame 58 comprises a rectangularly configured structure of cardboard, flexible plastic or the like having first 59 and second 60 sides and first 61 and second 62 edges, forming edge corners 63, 64.

The expansion frame 58 is configured to provide an aseptic means of opening the sleeve for allowing the depositing of the stethoscope in the sleeve, without the necessity of having to hold the mouth M of the sleeve 1 open manually.

The frame 58 may be configured in the periphery about the mouth M of sleeve 1, along the inside or outside wall of the sleeve, or may form a part of the wrapper, sheath, or dispenser with which sleeve 1 is packaged.

In use, the user merely applies transversal pressure 66, 65 directed against corners 63, 64, respectively, causing the frame to lift from its relatively flat, closed position 67, as shown in FIG. 1b, and expand to its relatively open position 68, as illustrated FIG. 1c.

Figure 2:
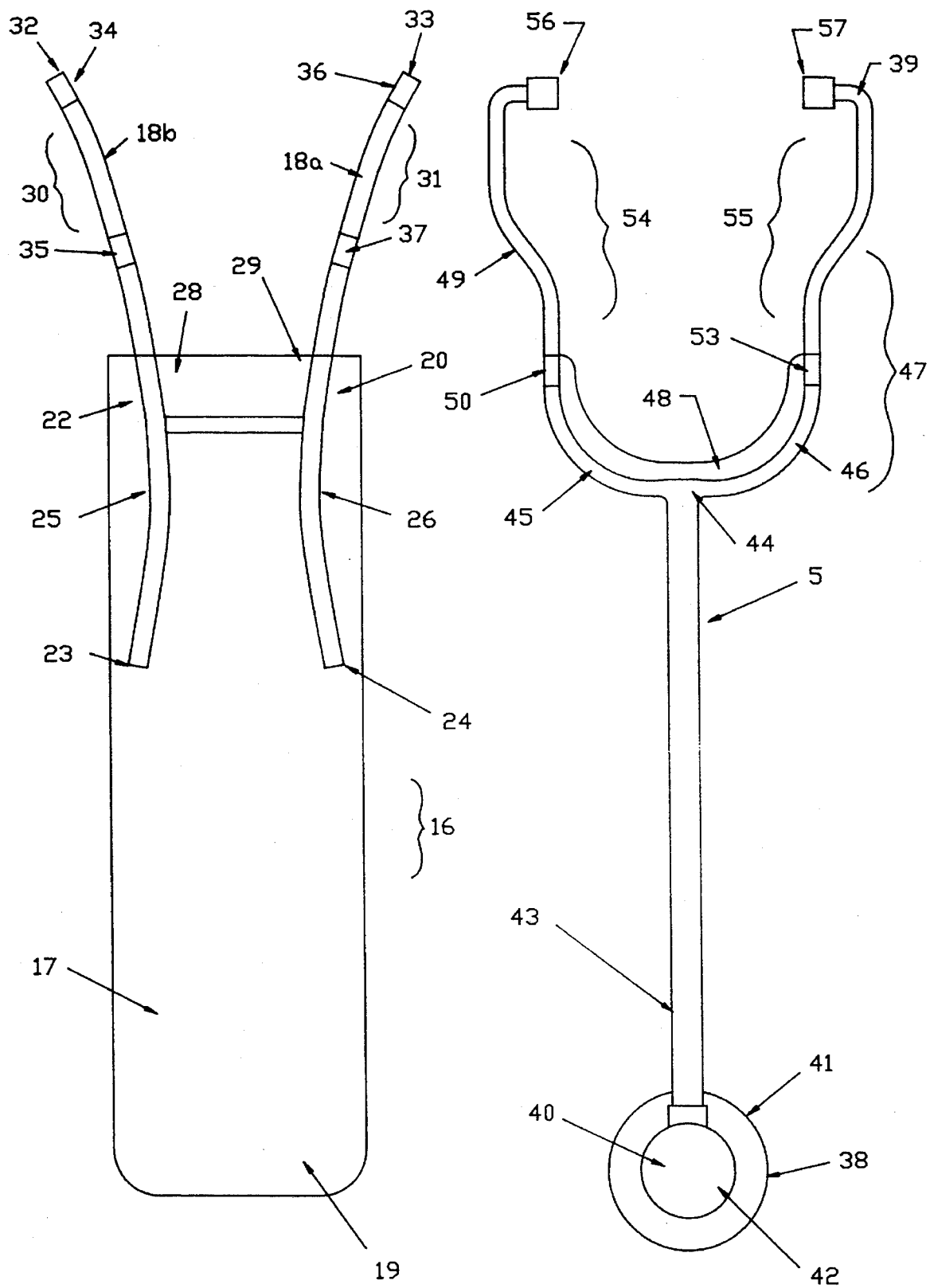
FIGS. 2a and 2b are frontal, partially cutaway views of an alternative embodiment of the stethoscope isolation system of FIG. 1, illustrating the sheath of the present invention in conjunction with the wishbone separation accessory of the present invention, and further illustrating an exemplary, off-the-shelf stethoscope.

Referring to FIGS. 1a and FIG. 2b, the stethoscope's S second 39, lower end 39 of the stethoscope S, including a head 40, grasping ring 42, diaphragm retaining ring 41 and sound tube 43, is lowered down into the cavity 4 formed in the sleeve 1 until the head 4 communicates with the first, closed end 19 of sleeve 17, and the second, open end 20 of sleeve communicates with the tube separation area 44.

It should be noted that stethoscope S may further include a spreader 48 joined (note areas 50, 53) to tubes 45, 46 for urging ear caps 56, 57 a specific distance apart. Tubes 45, 46 include curved portions 54, 55 for clearance about the user's head when the instrument is in use.

In use, the user merely removes the adhesive covering strip 14, folds over the strip at crease 15, over the spreader 48 and tube separation 44, to communicate with the first side 10, applying pressure to the adhesive 13 to affix the adhesive strip 6 to the first side 10 of the sleeve 1.

After the sleeve has been installed about the stethoscope S, the user may utilize the instrument in its normal fashion, placing the ear cups 56, 57 in the appropriate position and listening to the patient by grasping the head 40 via the grasping ring 42, and applying the diaphragm 41 to the desired area.

Once the examination is complete, the user merely grasps the end of strip 6 near the removable adhesive 13, pulling and thereby separating the strip from the first wall 10 of the sleeve, and slidingly disengaging the sleeve 1 from the stethoscope, disposing of it thereafter. Even though utilized in examining the patient, the head and sound tube 43 of the stethoscope S have not been in contact with the examined patient because of the presence of the sleeve 1, and thereby they remain uncontaminated and safe for use again with the next patient, wherein another, unused sleeve will be installed prior to examination.

Figure 3:
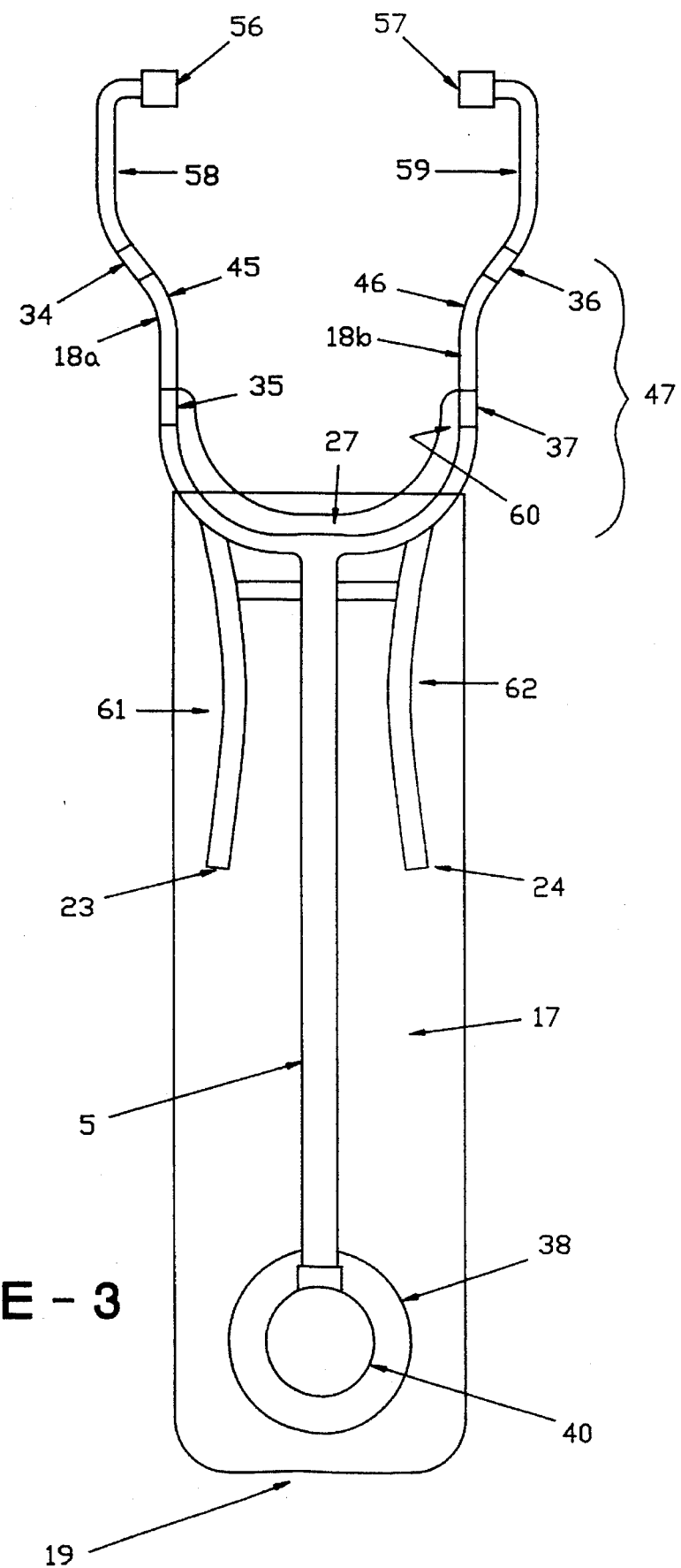
FIG. 3 is a frontal, partially cutaway view of the alternative embodiment of the present invention of FIG. 2a, wherein there is further shown the isolation system mounted to an off-the-shelf stethoscope.

FIGS. 2a and 3 illustrate an alternative embodiment of the present invention, designed for use in general duty as well as in isolation techniques, disposing with the need for a single stethoscope dedicated to a particular patient, while nonetheless providing a system which may be used with a dedicated instrument when desired.

The alternative embodiment of the present invention is designed to fully isolate all operations and contact of the stethoscope from the patient and health care worker, once the instrument has been placed in the isolation sleeve, preventing contamination during use of the instrument, further precluding cross contamination from one health care worker to another which might occur during non-examination contact with the instrument, such as during installation or removal from the user's person.

Like the preferred embodiment, the alternative embodiment 16 includes a sleeve 17 having a first, closed end 19 and a second, open end 20, but does not require the adhesive strap or strip as set forth in the preferred embodiment.

Affixed at points 28, 29 to the second, open end 20 of the sleeve at opposing upper side walls 22 are first (18a) and second (18b) spreading members, each spreading member having grasping handles 23, 24, curved area 25, 26, contact areas 30, 31, and upper ends 32, 33, respectively.

Situated at opposing ends of the contact areas 30, 31, respectively, are adhesive or wishbone joining straps 34, 35 and 36, 37.

FIG. 3 illustrates the use of the alternative embodiment 16 wherein it is installed in conjunction with an off-the-shelf, exemplary stethoscope S.

As shown, the first end 38 of the instrument is placed in the sleeve 17 until it communicates with the closed end 19 of the sleeve. Next, the first (18a) and second (18b) spreading members are affixed to the first (45) and second (46) sound tubes of the stethoscope S by wrapping (note 60) adhesive straps 34, 35 and 36, 37 to the sound tubes 45, 46, respectively, so that the sound tubes 45, 46 emanate from the medial opening 27 of the sleeve 17.

Spreading members 18a, 18b may be of an open tube design, wherein they have an open, radial area configured for somewhat enveloping the sound tubes 45, 46, if desired.

The stethoscope isolation system is now installed and ready for use.

In placing the protected instrument about the health care worker's neck or in communication with his or her ears, the user merely grasps the grasping handles 23, 24 under the sleeve 17, and presses them toward one another 61, 62, thereby increasing the distance 58, 59 between the ear caps 56, 57, and thereafter relieves pressure, allowing the wishbone construction 47 of the stethoscope to move the ear caps 56, 57 back toward one another, for communication with the user's ears or about the back of the user's neck.

During use, the user grasps the head 40 within the sleeve 17 and is then able to fully utilize the stethoscope S in normal fashion, yet without any contact to the patient or user, except for contact with the user's ears, a low risk contact which can be further remedied via the use of disposable ear plugs, if desired.

The embodiments described herein in detail for exemplary purposes are of course subject to many different variations in structure, design, application and methodology. For example, the adhesive taught as being utilized in conjunction with the adhesive strap may also comprise a hook and loop, "Velcro™" type arrangement, button and hole arrangement, or other removable attachment arrangement.

Because many varying and different embodiments may be made within the scope of the inventive concepts herein taught, and because many modifications may be made in the embodiments herein detailed in accordance with the descriptive requirements of the law, it is to be understood that the details herein are to be interpreted as illustrative and not in a limiting sense.

What is claimed is:

1. In association with the use of a medical stethoscope having a first, head end to be positioned during use in juxtaposition to a patient, a medial sound tube portion, a tube separation portion, and a second rear end comprising first and second ear tubes to be positioned during use in juxtaposition to each one of the user's ears, respectively, a method of preventing the passing of contamination between the patient and the user during the use of the medical stethoscope, comprising the following steps:

(a) providing a stethoscope isolation system to be used on the stethoscope during use of the stethoscope on the patient, including
   a sleeve having a first, closed end and a second, open end forming a mouth, and wall portions forming a cavity of sufficient size to allow the first, head end of the stethoscope to be placed therein, said sleeve having a sufficient length and scope to envelope the first, head end and the medial sound tube portion of the stethoscope, up to at least about the tube separation portion of the stethoscope, said sleeve being comprised of acoustically transparent, biologically impermeable material, and attachment means associated with said sleeve to at least temporarily attach the sleeve to the stethoscope while the stethoscope is in use on the patient;

(b) placing the first, head end of the stethoscope in said second, open end of said sleeve;

(c) moving the first, head end of the stethoscope into and through said cavity until the first, head end of the stethoscope is in juxtaposition to said first, closed end of said sleeve and at least the medial sound tube portion is substantially within said sleeve and is covered over by said sleeve up to at least about said tube separation portion; and (d) using said sleeve on the stethoscope to isolate, both directly and in reverse, the patient and the user from passing any contamination between them through mutual contact with the stethoscope while the stethoscope is in use on the patient.

2. The stethoscope contamination prevention method of claim 1, wherein in step "a" there is included the further step of:

providing a tab affixed at its proximal end to one part of said wall portions and having a length to reach through the tube separation portion of the stethoscope, as well as an opposing wall portion across said mouth of said sleeve when the first, head end and the medial sound tube portion of the stethoscope is in said sleeve; and wherein there is included, between steps "c" and "d", the following further steps:

(i) grasping said tab and extending it across said mouth of said sleeve, and about a portion of the tube separation portion of the stethoscope; and (ii) attaching the distal end of said tab to an opposing wall portion, affixing the sleeve to the stethoscope, said stethoscope enveloping the head end and medial tube portion of the stethoscope.

3. The stethoscope contamination prevention method of claim 2, wherein in step "ii" there-is included the step of:

using an adhesive to attach the distal end of said tab to said opposing wall portion.

4. The stethoscope contamination prevention method of claim 2, wherein in step "ii" there is included the step of:

using opposed, hook and loop material to attach the distal end of said tab to said opposing wall portion.

5. The stethoscope contamination prevention method of claim 2, wherein in step "i" there is included the step of:

extending said tab over said tube separation portion in attaching the distal end of said tab to said opposing wall portion.

6. The stethoscope contamination prevention method of claim 1, wherein there is included the further step of:

providing an expansion frame in association with said sleeve for expanding the mouth portion of said frame, said expansion frame being formed generally about the periphery of said mouth of said sleeve, said expansion frame further including first and second edge corners; and wherein in connection with step "b" there is included the further step of:

applying transverse pressure to said first and second edge corners of said expansion frame, opening said mouth of said sleeve for placing portions of said stethoscope in said sleeve.

7. The stethoscope contamination prevention method of claim 1, wherein in step "a" there is included the further step of:

providing spreader means for spreading the first and second ear tubes of the stethoscope, said spreader means situated in the cavity formed in said slip; and wherein there is provided the additional steps, after step "c", of i. attaching said spreader means to the first and second ear tubes of the stethoscope;

ii. grasping said slip over said spreader means;

iii. squeezing said slip over said spreader means, thereby separating the first second ear tubes of the stethoscope.

* * * * *